United States Patent [19]

Harvey

[11] Patent Number: 5,543,432
[45] Date of Patent: Aug. 6, 1996

[54] APPLICATION OF TRACE ELEMENTS TO ANIMALS

[76] Inventor: Colin M. Harvey, 44 Raymond Terrace, Birkenhead, Auckland, New Zealand

[21] Appl. No.: 334,223

[22] Filed: Nov. 4, 1994

[30] Foreign Application Priority Data

Nov. 8, 1993 [NZ] New Zealand ............................ 250163
May 31, 1994 [NZ] New Zealand ............................ 260638

[51] Int. Cl.⁶ ........................ A61K 31/16; A61K 31/135; A61K 31/13; A61K 31/11
[52] U.S. Cl. .......................... 514/630; 514/646; 514/667; 514/702
[58] Field of Search ................................... 424/630, 646, 424/667, 702

[56] References Cited

FOREIGN PATENT DOCUMENTS

| | | |
|---|---|---|
| 41516/78 | 6/1979 | Australia . |
| 90894/82 | 4/1985 | Australia . |
| 90937/82 | 1/1986 | Australia . |
| 12966/83 | 8/1987 | Australia . |
| 14363/88 | 8/1991 | Australia . |
| 20464/88 | 7/1992 | Australia . |
| WO93/07847 | 4/1993 | WIPO . |

OTHER PUBLICATIONS

CA 108:11251, Uchiumi, 1987.
CA 96:223016, Hausler, 1981.
CA 107:76766, Drake, 1986.
CA 119:188606, Wisniewski et al., Aug. 1993.

*Primary Examiner*—Kimberly Jordan
*Attorney, Agent, or Firm*—Young & Thompson

[57] ABSTRACT

A pour-on formulation containing a therapeutically effective amount of a trace element chosen from the group comprising selenium, copper, cobalt and iodine, in an aqueous or non-aqueous carrier. A non-aqueous formulation contains selenium dioxide dissolved in butyl dioxitol. An aqueous pour-on contains selenium selenate with keltrol, a wetting agent and water.

9 Claims, 2 Drawing Sheets

APPLICATION OF TRACE ELEMENTS TO ANIMALS

FIELD

This invention relates to the application of trace elements to animals.

BACKGROUND

The provision of trace elements to animals in order to supplement their diet, has been common practice. In some cases it is desirable to provide farm animals with trace elements, and in other cases it is essential if there is a mineral deficiency in the soil. Additional levels of trace elements have been included in animals diet or dosed by means of oral or parenteral administration. They have also been administered by means of various slow release boluses and long acting injectibles.

There is a need to provide an easy and effective means of administering trace elements to animals, preferably without the need to inject the animal, or to administer the material orally.

OBJECT

The present invention seeks to provide an improved means of administering trace elements to animals, or one which will at least provide farmers and veterinarians with a useful choice.

STATEMENT OF INVENTION

Surprisingly it has been discovered that trace elements can be administered to animals by means of pour-on formulations applied to the surface of an animal's skin, hide, or fleece.

In one aspect, the invention provides a pour-on formulation containing a therapeutically effective amount of a trace element in a pharmaceutically acceptable carrier.

In another aspect the invention provides a method of applying a trace element to an animal by topical application to achieve therapeutic serum levels of the trace element.

Preferably the pharmaceutically acceptable carrier is an alcohol, water, or combinations thereof.

Preferably the trace element is chosen from the group containing selenium, copper, cobalt and iodine.

More preferably the trace element is a water soluble trace element, and is present in a formulation containing water, a sticking agent, a wetting agent, and a dyestuff.

Alternatively, the formulation may comprise a co-solvent formulation containing a water soluble trace element such as sodium selenate, together with butyl dioxitol and water. In addition the formulation may contain an endoparasiticide, such as levamisole, synthetic pyrethroids, avermectin, abamectin, or the like, vitamins, such as Vitamin B12, dyestuff or other minor components. It may also contain at least one vitamin.

Other formulations can include non-aqueous formulations wherein the liquid carrier is an organic liquid. Examples include the alcohols, glycols or glycol esters; hydrocarbons such as xylene, paraffin or vegetable oils; isopropyl myristate; an ester of a fatty acid; an alkylamide of a fatty acid; an ethoxylated block polymer.

In another aspect the invention provides a non-aqueous formulation containing one or more oxides of selenium or copper or cobalt dissolved in a solvent chosen from the group comprising ethanol, monopropylene glycol, and butyl dioxitol. Preferably the trace element is present as selenium dioxide or selenium trioxide.

DRAWINGS

These and other aspects of the invention, will become apparent from the following description, which is given by way of example only, with reference to the accompanying drawings in which.

PREFERRED EMBODIMENTS

EXAMPLE 1

| Formulation 1 | % w/w |
| --- | --- |
| Sodium selenate | 2.0 |
| Keltrol | 0.3 |
| Wetting agent | 0.2 |
| Water | to 100 |

EXAMPLE 2

| Formulation 2 | % w/w |
| --- | --- |
| Sodium selenate | 1.2 |
| Butyl dioxitol | 30.0 |
| Water | to 100 |

EXAMPLE 3

| Formulation 3 | % w/w |
| --- | --- |
| Copper Chloride $2H_2O$ | 22.8 |
| Nonidet 620P | 10.0 |
| MPG | 10.0 |
| Formalin | 0.2 |
| Water | 57.0 |
| | 100 |

Formulation 3 is prepared by the following method:

To a clean dry mixing vessel, add the water, and with stirring, add Chloride $2H_2O$ and stir until dissolved. With stirring, add Nonidet 620P and MPG and stir until fully dispersed and lastly add Formalin.

EXAMPLE 4

| Formulation 4 | % w/w |
| --- | --- |
| Ammonium Sulphate | 0.50 |
| Citric Acid | 0.15 |
| Vitamin B12 (ex Roche) | 1.0 |
| Sodium Selenate | 1.18 |
| Butyl Dioxitol | 10.0 |
| Water | 87.17 |
| | 100.00 |

Example 4 is prepared by the following method:

Water was measured into a clean tank and ammonium sulphate and citric acid were added with the stirring. The vitamin B12 was added and stirred until fully dissolved. Sodium selenate was then added and stirred until fully dissolved. Lastly was added the butyl dioxitol and the solution was mixed until uniform.

EXAMPLE 5

| Formulation 5 | % w/v |
| --- | --- |
| Selenium Dioxide (SeO$_2$) | 0.71 |
| Butyl Dioxitol | to 100 mL |

To produce a selenium pour-on containing 5 grams of selenium per liter, the selenium dioxide is stirred into the butyl dioxitol until fully dissolved (approximately 30 minutes). This makes a non-aqueous pour-on formulation.

Other non-aqueous formulations can be made using a solvent chosen from a group comprising monopropylene glycol, ethanol, and butyl dioxitol. We have found that selenium dioxide, selenium trioxide, and H$_2$SeO$_4$ are all soluable at this class of solvents, and they are all useful solvents which can be used as pour-on formulations.

Trace elements, can be added to pour-on formulations containing other active ingredients, for example pour-ons containing anthelmintics such as moxidectin, or any of the avermectins, for example ivamectin.

Formulation 6 has been the subject of a product stability trial, and this is shown in table 6. This table shows that the product is stable, and contains useful mounts of selenium after three months.

TRIAL 1

Figure 1:
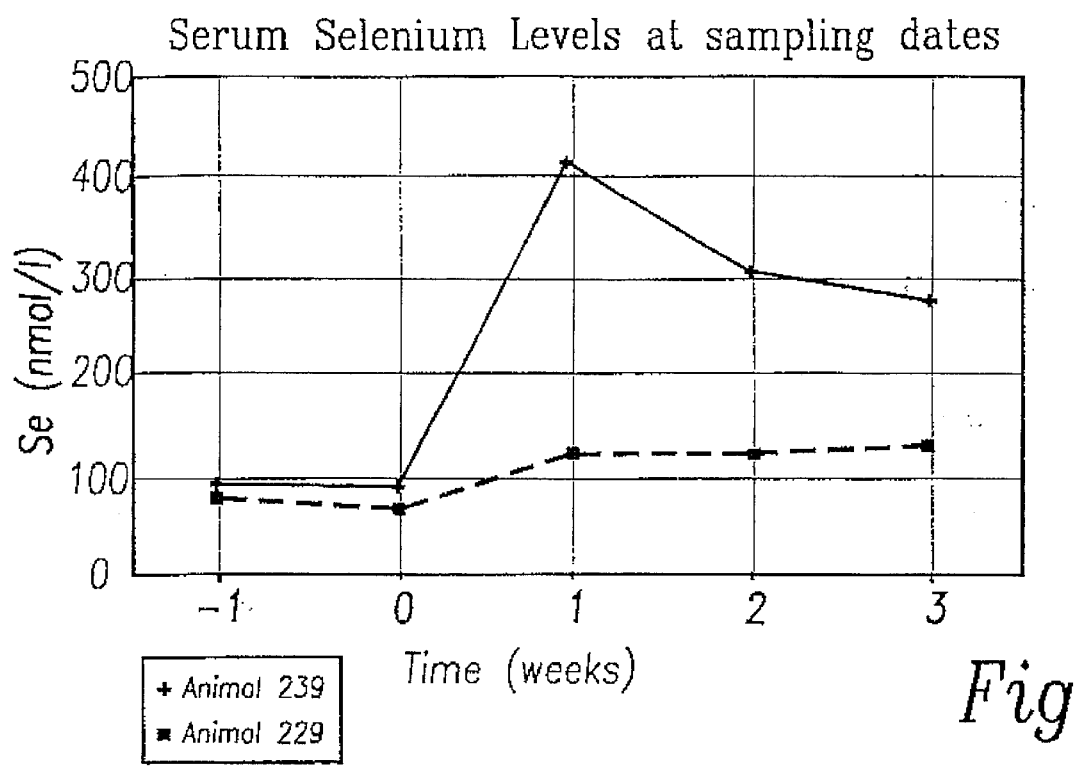
FIG. 1 is a graph showing serum selenium levels, formulation 1, in animals.

Formulation 1 was trialled on two friesian bulls with the result shown in Table 1 and FIG. 1.

This trial of Formulation 1 was conducted to determine whether sodium selenate can be successfully absorbed through the skin following the application of a topical ("pour-on") formulation.

Materials and Methods

Two Friesian yearling bulls were weighed and examined to confirm the absence of any back skin defects. Using a critical trial format whereby each animal acted as its own control, the two bulls were then treated with a pour-on formulation of the test product. This was administered along the back mid-line with a graduated syringe. The bulls were grazed normally over the trial period.

The test product was a 0.8% solution of elemental selenium (ie. sodium selenate) at 8 mg/ml in accordance with Formulation 1. The normal oral dose is 20–30 mg/kg of selenium. Accordingly, it was decided to apply the test product at double the adult dose, or 60 mg/kg of selenium. This equated to a volume of 7.5 ml of test product.

The two bulls were bled twice prior to treatment, and the serum selenium levels are shown in Table 1, and plotted in FIG. 1. Both were treated on the same start date (time 0 in FIG. 1) and then re-bled at one, two and three weeks post treatment. The sera was removed and frozen and subsequently analysed for selenium levels.

Results

The test material (coloured blue) was very viscous and it seemed not to penetrate the hair mat to reach the skin surface. The following day the test material still seemed to remain on top of the hair mat.

Table 1 gives the results of the changes in serum levels of selenium for both trial animals. The selenium status of both animals was significantly raised (P,0.01) by the treatment. Normal serum selenium levels are typically greater than 150 nmol/l, whereas the selenium levels in Table 1 and shown graphically in FIG. 1 were significantly above this level for animal 239.

TABLE 1

| | | | Serum Selenium Levels at Sampling Dates (nmol/l)* | | | | |
| --- | --- | --- | --- | --- | --- | --- | --- |
| Animal Number | Weight (kg) | Volume of Test Product (ml) | 27.7 Day −7 | 3.8 Day 0 | 10.8 Day 7 | 17.8 Day 14 | 24.8 Day 21 |
| 229 | 335 | 7.5 | 79 | 68 | 120 | 120 | 130 |
| 239 | 315 | 7.5 | 93 | 89 | 420 | 310 | 280 |

*Normal serum selenium levels are >150 nmol/l

Discussion

The application of the test product markedly raised the serum selenium levels of both treated animals in comparison to their pre-treatment level. Although each animal was treated with the same volume of material and each was approximately the same weight, the serum responses vary markedly in magnitude, as well as time to peak. These variations in rate and absorption may relate to the viscosity of the test product and the individual physical hair factors. The weather throughout the trial period was warm and dry for the time of year. Certainly no rain fell on the animals for at least four days post-treatment. Prior to treatment and for 24 hours both bulls were under cover to ensure this aspect of coat dryness.

This pilot trial demonstrates that sodium selenate can be formulated to be successfully absorbed through the skin following topical application.

TRIAL 2

A trial was carried out on a number of animals to compare the serum levels from a selenium injection (Se-Hypo as the control) with formulation (2) at rates of 12 ml and 18 ml of pour-on (equivalent to 60 mg/kg and 90 mg/kg of selenium respectively).

Materials and Method

Twelve friesian weaned bulls having an average weight of 231 kgs and having low serum selenium levels were randomly allocated to one of three groups. The four animals in one group were each injected with 30 mg/kg of Se-Hypo. Animals in the other two groups were treated with formulation (2) at 60 mg/kg and 90 mg/kg respectively.

Serum selenium levels were measured prior to treatment and then weekly for nine weeks. On day 0 there was no significant difference between the three groups (means range 70–85 nmol/l). After seven days the mean serum selenium levels of the groups receiving topical application were higher than for the control group (535 and 700 nmol/l respectively compared to 513 nmol/l in the control group).

Table 2 gives the results of the changes in serum selenium levels from day 0 (treatment day) to day 63.

Discussion

Figure 2:
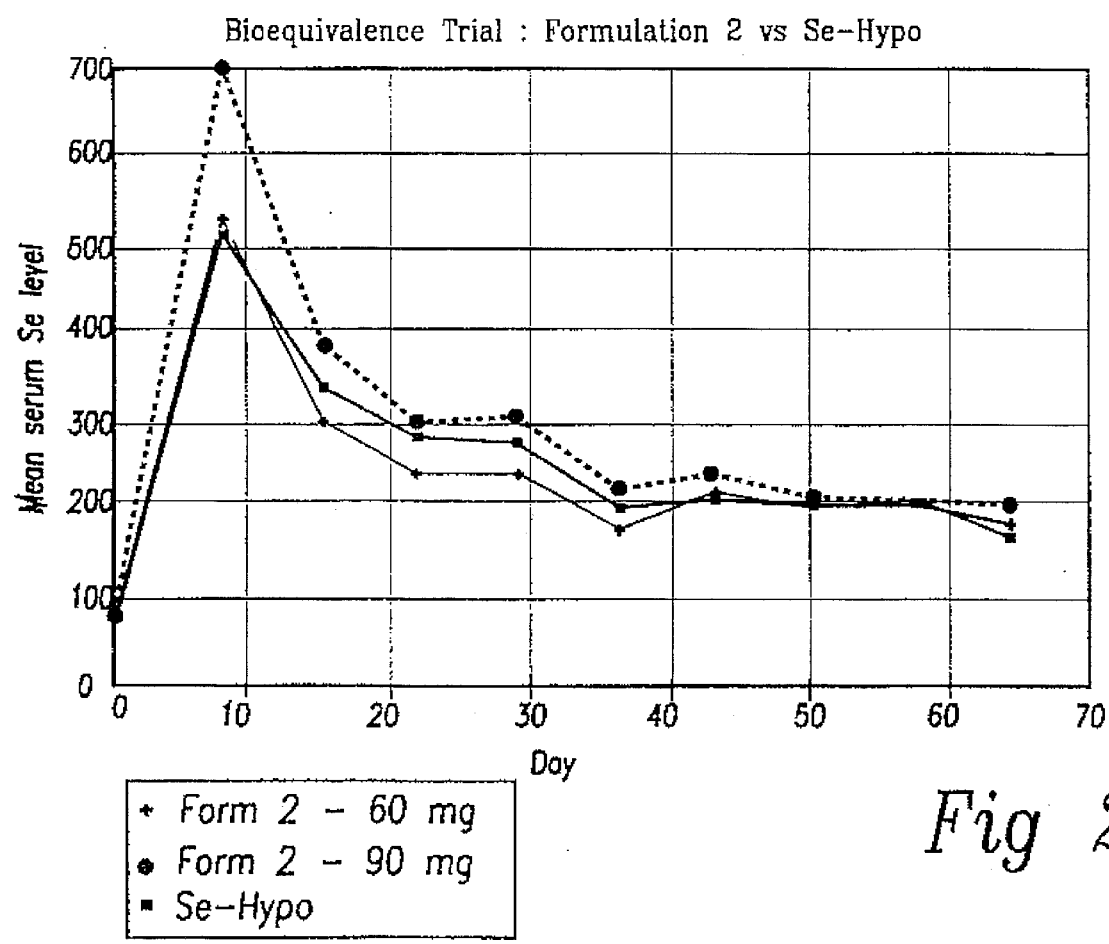
FIG. 2 is a graph showing mean serum selenium levels, formulation 2, in animals.

From Table 2 it can be seen that the serum selenium levels peaked on day 7 and declined steadily until day 35 when all three groups reached a plateau,—see (FIG. 2).

None of the animals receiving topical application displayed any sensitivity or toxicity towards the pour-on formulation. The pour-on formulation is easy to apply to the animals and overcomes the need to inject individual animals.

Over the 63 day trim period the 60 mg/kg pour-on produced a serum response that was bio equivalent to the 30 mg/kg dose of injected Se-Hypo. The 90 mg/kg pour-on was seen to be superior to the control.

It can be concluded that at both 60 mg/kg and 90 mg/kg the pour-on formulation (2) was very effective in raising serum selenium levels.

A group of 29 jersey bulls aged 18 months were weighed and randomly divided into three groups comprising 10, 9 and 10 animals. Each group was allocated one of the following treatments:

Cuprax (10)

Untreated controls (9)

Formulation 3 (10)

The 29 animals were all treated at the same time and for the following week no rain was recorded as possibly affecting the group 3 response. Each animal given Cuprax was treated with two 10 g capsules according to the manufacturer's instructions.

Formulation 3 was administered at 1 ml per 20 kg poured along the midline back region.

All the animals were grazed normally for the three week duration of the trial.

Three weeks after treatment, the bulls were all slaughtered for human consumption and samples of liver were removed from each animal. Each liver was separately sampled in 4 remote places. Two of the samples from each animal were analysed and the results averaged. The results were analysed statistically using a one-way analysis of variants and pair-wise comparison of means.

Results

Table 3 gives individual results and group means. There was no statistical difference recorded between any of the group means, but it is noteworthy that the highest mean liver copper level was recorded for the group given formulation 3.

The topical formulation produced severe skin abrasion along the midline back. This did not appear to cause the animals any distress and did not subsequently lead to any downgrading of the hide at slaughter time.

TABLE 2

| Animal No. | Weight (kg) | Treatment* | Serum Selenium (nmol/l). Days Post-Treatment | | | | | | | | | |
|---|---|---|---|---|---|---|---|---|---|---|---|---|
| | | | 0 | 7 | 14 | 21 | 28 | 35 | 42 | 49 | 56 | 63 |
| 6 | 235 | Se-Hypo | 86 | 490 | 340 | 290 | 270 | 210 | 220 | 220 | 220 | 180 |
| 20 | 223 | Se-Hypo | 76 | 520 | 340 | 280 | 320 | 210 | 210 | 210 | 190 | 180 |
| 12 | 245 | Se-Hypo | 69 | 480 | 310 | 250 | 240 | 190 | 180 | 180 | 190 | 170 |
| 7 | 195 | Se-Hypo | 86 | 560 | 350 | 300 | 270 | 190 | 230 | 220 | 230 | 220 |
| | | mean | 79 | 513 | 335 | 280 | 285 | 200 | 210 | 208 | 208 | 188 |
| 29 | 222 | A12 | 61 | 550 | 300 | 240 | 220 | 160 | 200 | 180 | 250 | 160 |
| 42 | 247 | A12 | 71 | 500 | 290 | 230 | 240 | 200 | 210 | 190 | 190 | 170 |
| 27 | 236 | A12 | 64 | 590 | 320 | 250 | 280 | 190 | 210 | 210 | 190 | 170 |
| 23 | 271 | A12 | 82 | 500 | 270 | 210 | 200 | 140 | 180 | 160 | 180 | 160 |
| | | mean | 70 | 535 | 295 | 233 | 235 | 173 | 200 | 185 | 203 | 165 |
| 10 | 194 | A18 | 76 | 770 | 400 | 270 | 260 | 190 | 190 | 200 | 190 | 180 |
| 9 | 245 | A18 | 120 | 660 | 400 | 330 | 370 | 240 | 290 | 230 | 260 | 140 |
| 35 | 227 | A18 | 63 | 650 | 340 | 300 | 290 | 220 | 230 | 200 | 190 | 200 |
| 15 | 232 | A18 | 79 | 720 | 400 | 300 | 300 | 240 | 240 | 230 | 220 | 190 |
| | | mean | 85 | 700 | 385 | 300 | 305 | 223 | 238 | 215 | 215 | 178 |

*Se-Hypo given at 6 ml (30 mg). Formulation (2) test product at rates of 12 and 18 ml equivalent to 60 and 90 mg respectively.

TRIAL 3

Formulation 3 was trialled on jersey bulls with the results shown in Table 3.

This trial of formulation 3 was conducted to determine whether a copper salt could be successfully and safely absorbed through the skin following the application of a topical ("pour-on") formulation, to raise liver copper levels.

Materials and Methods

TABLE 3

Liver Copper Levels in Individual Animals and Group Means

| Animal No. | Control | Animal No. | Cuprax | Animal No. | Test Product |
|---|---|---|---|---|---|
| 032 | 382 | 108 | 702 | 010 | 298 |
| 148 | 606 | 078 | 788 | 164 | 1133 |
| 111 | 280 | 016 | 952 | 289 | 570 |
| 154 | 119 | 290 | 310 | 101 | 632 |

TABLE 3-continued

Liver Copper Levels in Individual Animals and Group Means

| Animal No. | Control | Animal No. | Cuprax | Animal No. | Test Product |
|---|---|---|---|---|---|
| 342 | 786 | 212 | 1093 | 240 | 959 |
| 119 | 749 | 054 | 783 | 367 | 1378 |
| 089 | 487 | 022 | 867 | 139 | 293 |
| 170 | 1149 | 359 | 278 | 153 | 884 |
| 272 | 1178 | 021 | 469 | 338 | 641 |
|  |  | 091 | 630 | 120 | 725 |
| mean | 636 | mean | 687 | mean | 751 |

Discussion

The fact that the topical test formulation produced a higher mean liver copper level within the first three weeks would suggest that topical application can provide animals successfully with supplementary copper. The main problem associated with formulation 3 was the toxicity at the site of application.

Formulation 3 delivered 5 mgs of copper per kg. The maximum comparable rate for a parenteral copper product is approximately 1 mg per kg. The dose rate for topically applied chemicals is typically greater than that for oral or parenteral formulations but not usually by a factor of 5 (e.g. ivomec×2.5). It may therefore be possible to combine a lower dose rate (mg/kg) and increased volume to reduce the toxic effects without jeopardising the effectiveness of the treatment.

In conclusion, the test product appeared to successfully raise liver copper levels above those of the untreated controls.

TRIAL 4

A trial was conducted was low blood selenium cattle (limousin heifers 12 months old). This trial compared the pour-on formulation (2) at a lower dose rate than in trial 2 with Se-Hypo. The results are as shown in Table 4.

Materials and Method

The pour-on formulation (2) was administered at a rate of 6 mls per 100 kg. This effectively applies 30 mg per kg of selenium on the backline of cattle. Se-Hypo was administered at the rate of 2 mls per 100 kg. This effectively supplies 10 mg per 100 kg subcutaneously.

The cattle were bled prior to the commencement of the trial and then placed in 3 groups on the basis of their blood selenium levels.

1. Group controls (6)
2. Se-Hypo (7)
3. Formulation 2 of selenium (7)

The cattle were bled at 2, 4 and 8 weeks post treatment. The blood levels were monitored and the cattle were retreated in the treatment group nine weeks after the commencement of the trial.

TABLE 4

|  | START 7/1/94 | FEB 9 | FEB 26 | MAR 10 | MAR 31 |
|---|---|---|---|---|---|
| CONTROL | | | | | |
| Tag 15 | 260 | 300 | 210 | 340 | 520 |
| Tag 16 | 240 | 220 | 200 | 290 | 460 |
| Tag 21 | 200 | 200 | 290 | 320 | 410 |
| Tag 24 | 240 | 250 | 300 | 400 | 410 |
| Tag 29 | 240 | 250 | 190 | 370 | 490 |
| Tag 33 | 240 | 260 | 310 | 310 | 450 |
| Average | 237 | 247 | 250 | 338 | 457 |

TABLE 4-continued

|  | START 7/1/94 | FEB 9 | FEB 26 | MAR 10 | MAR 31 |
|---|---|---|---|---|---|
| SELJECT | | | | | |
| Tag 13 | 290 | 560 | 480 | 670 | 1000 |
| Tag 20 | 230 | 580 | 550 | 590 | 960 |
| Tag 23 | 220 | 550 | 540 | 1600* | 1100 |
| Tag 27 | 250 | 580 | 490 | 620 | 910 |
| Tag 28 | 180 | 550 | 440 | 590 |  |
| Tag 32 | 180 | 530 | 460 | 520 | 850 |
| Tag 36 | 220 | 560 | 420 | 570 | 920 |
| Average | 224 | 559 | 483 | 593 | 957 |
| FORMULATION 2 | | | | | |
| Tag 17 | 330 | 500 | 580 | 490 | 820 |
| Tag 19 | 230 | 790 |  | 650 | 1200 |
| Tag 22 | 230 | 550 | 500 | 530 | 930 |
| Tag 25 | 290 | 650 | 520 | 660 | 1000 |
| Tag 26 | 230 | 900 | 710 | 870 | 1200 |
| Tag 30 | 230 | 670 | 400 | 830 | 920 |
| Tag 35 | 210 | 770 | 630 | 740 | 1000 |
| Average | 250 | 690 | 557 | 681 | 1010 |

*Injected in error before bleeding (5 minutes)
NOTE: All units above ae whole blood selenium as nmol/l

TRIAL 5

A trial was conducted on twenty clinically healthy 18 months old Angus cattle.

Materials and Methods

The cattle were bled prior to the commencement of the trial and then randomly place in one of the following groups:

Group 1: Test animals treated with our selenium pour-on formulation #2 (as described in Example 2) (contains 5 mg/ml selenium as sodium selenate at the proposed label dose rate of 1.5 m./50 kg body weight)

Group 2: Test animals treated with Se-Hypo (contains 5 mg/ml selenium as sodium selenate at the label dose rate of 5 ml injection per cattle).

The cattle were bled at 4 and 12 weeks post treatment and samples sent to the MAP Quality Management Laboratory Lincoln.

Assessment

Assessment was made on the basis of selenium blood levels (nmol/l) of treated animals.

Results

Figures 3, 4:
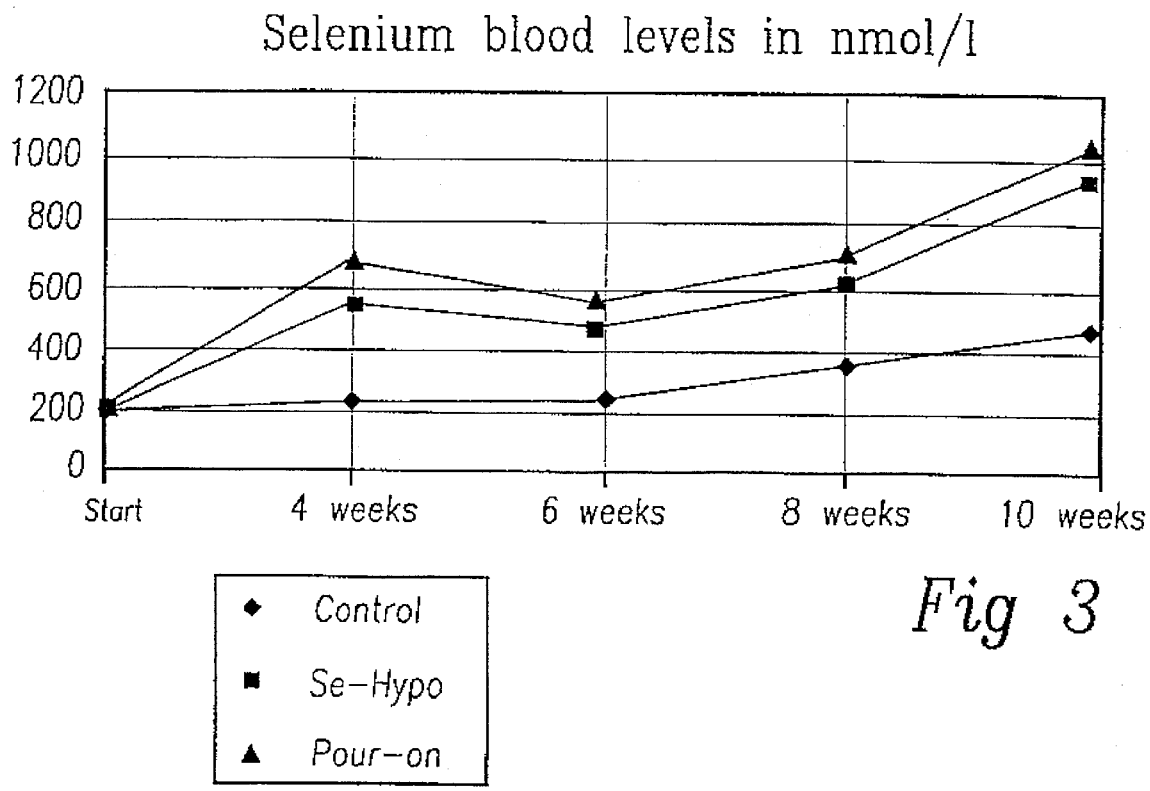
FIG. 3 is a graph showing selenium blood levels, formulation 2, in animals.
FIG. 4 is a graph showing blood selenium levels in Angus cattle during trial 5, using formulation 2 over a 12 week period.

The results are outlined in Table 5 and FIG. 4.

Blood samples were blinded and selenium levels tested by MAF Quality Management Laboratory Lincoln.

Animals treated with both our selenium pour-on and Se-Hypo obtained a rise in blood selenium levels when measured at 4 weeks post-treatment. This rise was maintained and slightly increased at second testing (12 weeks) which indicates a long term benefit of our selenium pour-on and Se-Hypo treatments in selenium deficiency and related diseases in cattle.

TABLE 5

Blood selenium levels in cattle in nmol/l. Reference values are:
Responsive < 130; Marginal 130–250; Adequate 250–2000
(MAF Quality, Lincoln)

| Animal No. | Initial Results 8.4. | One month 12.5. | Three month 13.7. |
|---|---|---|---|
| 31 | 1000 | 1420 | 1410 |
| 32 | 560 | 1120 | 1200 |
| 33 | 860 | 1370 | 1470 |
| 34 | 510 | 1060 | 960 |

TABLE 5-continued

Blood selenium levels in cattle in nmol/l. Reference values are:
Responsive < 130; Marginal 130–250; Adequate 250–2000
(MAF Quality, Lincoln)

| Animal No. | Initial Results 8.4. | One month 12.5. | Three month 13.7. |
|---|---|---|---|
| 35 | 610 | 1060 | 1130 |
| 36 | 500 | 1060 | 1380 |
| 37 | 500 | 1180 | 1600 |
| 38 | 440 | 1260 | 1420 |
| 39 | 960 | | |
| 310 | 490 | 970 | 1180 |
| Mean Selpor | 643 | 1166 | 1305 |
| STD | 201 | 145 | 188 |
| 311 | 580 | 1220 | 1320 |
| 312 | 1060 | | |
| 313 | 380 | 1030 | 1440 |
| 314 | 930 | 1440 | 1810 |
| 315 | 830 | 1240 | 1300 |
| 316 | 490 | | |
| 317 | 570 | 1190 | 1320 |
| 318 | 560 | 960 | 1120 |
| 319 | 970 | 1530 | 1790 |
| 320 | 410 | 1010 | 1190 |
| Mean Se-Hypo | 678 | 1202 | 1411 |
| STD | 234 | 190 | 241 |

Animals 31–310 Selenium pour-on treatment
Animals 310–320 Se-Hypo treatment

Conclusion

The pour-on formulation when applied at the rate of 6 mls per 100 kg gave blood selenium levels that were similar in effect on low blood selenium cattle to the levels produced by treating cattle with Se-Hypo (see FIG. 3).

Whilst these examples have been given as illustrative of the invention, the invention is not limited to the examples and other alterations and modifications can be made to the foregoing such as the addition of other adjunctive compounds that can be administered topically without departing from the scope of this invention as claimed.

I claim:

1. A pour-on formulation containing a therapeutically effective amount of a trace element in a pharmaceutically acceptable carrier, wherein the formulation is a non-aqueous formulation containing one or more oxides of selenium or copper or cobalt dissolved in a solvent chosen from the group consisting of ethanol, monopropylene glycol and butyl dioxitol.

2. A formulation as claimed in claim 1 wherein the trace element is present as selenium dioxide or selenium trioxide.

3. A method of raising the serum levels of a trace element in animals by topically applying to the animal a pour-on formulation containing a therapeutically effective amount of a trace element in a pharmaceutically acceptable carrier.

4. A method as claimed in claim 3 wherein the trace element is selected from the group consisting of selenium, copper, cobalt and iodine.

5. A method as claimed in claim 4 wherein the pharmaceutical carrier is an organic liquid.

6. A method as claimed in claim 4 wherein the pharmaceutical carrier is water or in combination with water.

7. A method as claimed in claim 3 wherein the formulation is a non-aqueous formulation containing one or more oxides of selenium or copper or cobalt dissolved in a solvent chosen from the group consisting of ethanol, monopropylene glycol and butyl dioxitol.

8. A method as claimed in claim 7 wherein the trace element is present as selenium dioxide or selenium trioxide.

9. A method as claimed in claim 3 further including at least one endoparasiticide or at least one vitamin.

* * * * *